United States Patent [19]

Husbands et al.

[11] Patent Number: 5,512,574
[45] Date of Patent: Apr. 30, 1996

[54] QUINUCLIDINE AND AZABICYCLO [2.2.1] HEPTANE PYRAZINYL ETHERS AS MUSCARINIC AGONISTS

[75] Inventors: George E. M. Husbands, Berwyn; Joseph Tokolics, King of Prussia, both of Pa.

[73] Assignee: American Home Products Corporation, Madison, N.J.

[21] Appl. No.: 414,406

[22] Filed: Mar. 31, 1995

Related U.S. Application Data

[63] Continuation-in-part of Ser. No. 360,905, Dec. 21, 1994, abandoned.

[51] Int. Cl.$^6$ .................. A61K 31/495; C07D 453/02
[52] U.S. Cl. .................. 514/253; 544/408; 546/112; 546/137
[58] Field of Search .................. 544/408, 405; 514/253

[56] References Cited

U.S. PATENT DOCUMENTS 5,082,843  1/1992  Cliffe .................. 514/253

FOREIGN PATENT DOCUMENTS 458214  5/1991  European Pat. Off. .
3839385  5/1990  Germany .

OTHER PUBLICATIONS

Quirion et al, *TIPS*, pp. 80–84, (1989).
Street et al. *J. Med. Chem.* 35 pp. 295–305 (1992).
Ward et al, *J. Med. Chem.* 35 pp. 4011–4019 (1992).

*Primary Examiner*—Emily Bernhardt
*Attorney, Agent, or Firm*—Richard K. Jackson

[57] ABSTRACT

The compound of the formula:

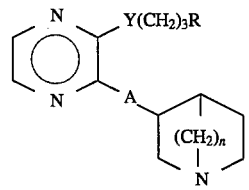

in which Y is oxygen or sulfur; A is oxygen, sulfur or $-NR_2$, where $R_2$ is hydrogen or alkyl; R is $-CH_2CH_3$, $-CH_2CH_2CH_3$, $-CH(CH_3)_2$, $-CH_2CH(CH_3)_2$, $-CH_2CF_3$, $-CH_2CH_2CF_3$, $-CH(CF_3)_2$, $-CH_2CH(CF_3)_2$, $-C_3H_5$, $-CH_2C_3H_5$, $-CH_2CH_2C_3H_5$, $-C_4H_7$, $-CH_2C_4H_7$, $-C_5H_9$, $-CH_2C_9$, $-C_6H_{10}$, $-CH_2C_6H_{10}$, $-C_4H_3S$, $-CH_2C_4H_3S$, $-C_6H_5$ or $-CH_2C_6H_5$; and n is one of the integers 1 or 2; or a pharmaceutically acceptable salt thereof are centrally active muscarinic agents.

23 Claims, No Drawings

QUINUCLIDINE AND AZABICYCLO [2.2.1] HEPTANE PYRAZINYL ETHERS AS MUSCARINIC AGONISTS

RELATED APPLICATION

This application is a continuation-in-part of U.S. patent application Ser. No. 08/360,905, filed Dec. 21, 1994, by G. E. M. Husbands and J. Tokolics, now abandoned.

BACKGROUND OF THE INVENTION

Street et al., J. Med. Chem. 35, 293–305 (1992) disclose the cortical muscarinic activity of a group of quinuclidinyl and 1-azanorbonyl pyrazine derivatives.

DE 3839385 discloses some alkyl, alkenyl or alkinyl ether derivatives of quinuclidine as muscarinic receptor agonist s.

E.P. 0,458,214 discloses variously substituted ethers of 1-azabicyclic alkanes as muscarinic agonists.

U.S. Pat. No. 5,082,843 discloses a series of N-heteroaryl ethers of azabicyclic alkanes as $5-HT_3$ antagonists.

Ward et al., J. Med. Chem. 35,4011 (1992) disclose a series of 3-(3-substituted-pyrazinyl)-1,2,5,6-tetrahydro-1-methylpyridines having high affinity for the central muscarinic receptors.

DESCRIPTION OF THE INVENTION

In accordance with this invention there is provided a group of compounds of the formula:

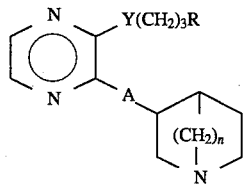

in which Y is oxygen or sulfur;
  A is oxygen, sulfur or $-NR_2$, where $R_2$ is hydrogen or alkyl of 1 to 6 carbon atoms;
  R is $-CH_2CH_3$, $-CH_2CH_2CH_3$, $-CH(CH_3)_2$, $-CH_2CH(CH_3)_2$, $-CH_2CF_3$, $-CH_2CH_2CF_3$, $-CH(CF_3)_2$, $-CH_2CH(CF_3)_2$, $-C_3H_5$, $-CH_2C_3H_5$, $-CH_2CH_2C_3H_5$, $-C_4H_7$, $-CH_2 C_4H_7$, $-C_5H_9$, $-CH_2C_5H_9$, $-C_6H_{10}$, $-CH_2C_6H_{10}$, $-C_4H_3S$, $-CH_2C_4H_3S$, $-C_6H_5$ or $-CH_2C_6H_5$;
and n is one of the integers 1 or 2;
or a pharmaceutically acceptable salt thereof.

The compounds of this invention exist as the free bases and pharmaceutically accepted salts of both the racemic forms and their individual enantiomers. Of these compounds, it is preferred that A and Y are oxygen or sulfur, R is propyl, and n is 1. The most preferred compounds of the endo series are the levo isomer where A is oxygen and Y is sulfur and the dextro isomer where both A and Y are oxygen. In the exo series, the most preferred compounds are the dextro isomer where A is oxygen and Y is sulfur. Both the stereo and optical isomers can be isolated by conventional means or prepared by selective synthesis.

The pharmaceutically acceptable salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids.

The substituted pyrazine compounds of this invention stimulate central muscarinic acetylcholine receptors and are therefore useful in the treatment of neurological and mental illnesses related to cholinergic deficiency. Such diseases include presenile and senile dementia (also known as Alzheimer's Disease and Senile Dementia of the Alzheimer Type, respectively), Huntington's Chorea, Tardive Dyskinesia, Hyperkinesia, Mania and Tourette's Syndrome. Alzheimer's Disease is a slowly progressive neurological disorder characterized by deficits in cognitive function including memory, attention, language and visual perception capabilities. Both the racemates and their individual enantiomers bind to muscarinic acetylcholine receptors, and show $M_1$ agonist activity in assays involving phosphoinositide turnover in CHO cells and they possess receptor selectivity in standard test procedures involving the use of cyclic AMP.

The compounds of this invention are prepared by either of the following procedures (1)

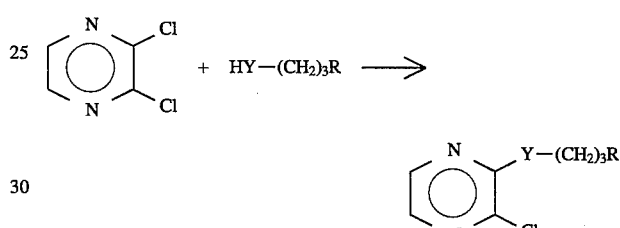

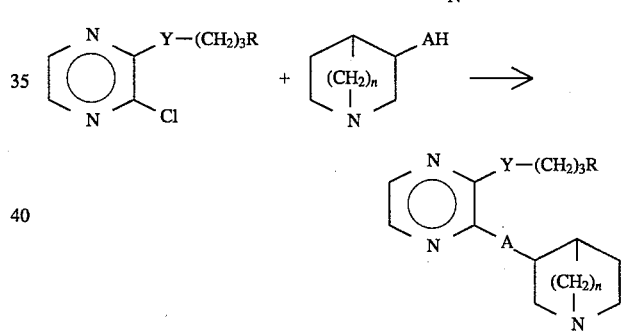

(2)

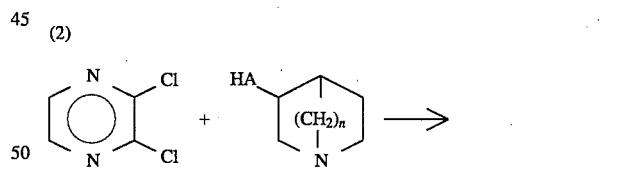

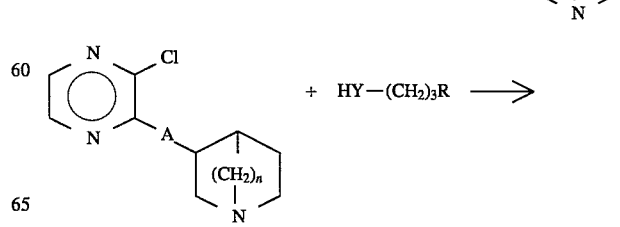

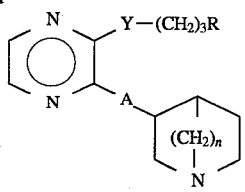

Method 1 is the preferred method for the preparation of the pure enantiomers. Since the azabicyclic alcohols can be resolved by crystallization with molar equivalents of (+) or (−) tartaric acid and the purified enantiomers used in the scheme. Method 2 was used for the initial preparation of the preferred compound (Example 2(−)) which was then resolved by HPLC.

The following Examples illustrate the preparation techniques employed in the production of the compounds of the invention.

EXAMPLE 1

(±)-(endo)-3-(3-Hexyloxy-pyrazin-2-yloxy)-1-aza-bicyclo[2.2.1]heptane

A solution of racemic (endo)-1-azabicyclo[2.2.1]heptan-3-ol (3.4 g, 30 mmole) in dry DMF (35 mL) was added to a suspension of sodium hydride (0.82 g, 33 mmole) in dry DMF (20 mL) and the mixture stirred for 30 minutes. A solution of 2,3-dichloropyrazine (4.4 g, 30 mmole) in DMF (15 mL) was added and the mixture stirred at room temperature for 2 hours. Isopropanol (5 mL) was added and the solvents evaporated. The residue was purified by column chromatography on silica gel using varying concentrations of methanol in chloroform. Fractions containing the desired product were evaporated, yielding (+)-(endo)-3-(3-chloro-pyrazine-2-yloxy)-1-aza-bicyclo[2.2.1heptane as an oil.

Yield 6.2 g, Mass spectral analysis: Molecular weight by Chemical Ionization [M+H]$^+$ M/Z 226/228 with detected chlorine isotope pattern.

A solution of sodium hexyloxide was generated by adding sodium (0.3 g, 1.3 mmole) to hexyl alcohol (50 mL) and warming to 60° for one hour. The reaction mixture was cooled and a solution of (endo)-3-(3-chloro-pyrazin-2-yloxy)-1-azabicyclo[2.2.1]heptane (3.0 g, 13 mmole) in hexyl alcohol (10 mL) added. The mixture was heated at 60° C. for two hours. The solvent was evaporated and the residue purified using column chromatography on silica gel with varying concentrations of methanol in chloroform. The product was dissolved in diethyl ether and the solution saturated with HCl gas. The hydrochloride salt of the title compound obtained was crystallized from ethyl acetate/methanol, m.p. 140°–142° C.

Elemental analysis for $C_{16}H_{25}N_3O_2.HCl$ Calculated: C, 58.62; H, 7.99; N, 12.82 Found: C, 58.36; H, 8.08; N, 12.85

EXAMPLE 2

(endo)-3-(3-Hexylsulfanyl-pyrazin-2-yloxy)-1-aza-bicyclo[2.2.1]heptane

A solution of (endo)-3-(3-chloropyrazin-2-yloxy)-1-azabicyclo[2.2.1]heptane (2.2 g, 10 mmole) in DMF (5 mL) was added to a suspension of sodium hexanethiolate prepared from sodium hydride (0.24 g, 10 mmole) and hexanethiol (1.2 g, 10 mmole) in THF (25 mL). After two hours of continuous stirring at room temperature, isopropanol was added and the solvents were evaporated. Column chromatography on silica gel (chloroform/methanol) yielded the pure product. It was dissolved in diethyl ether saturated with HCl gas, affording the title compound as the hydrochloride salt, m.p. 186°–188° C.

Elemental Analysis for $C_{16}H_{25}N_3OS.HCl$ Calculated: C, 55.88; H, 7.62; N, 12.22 Found: C, 55.85; N, 7.77; N, 12.19

The racemic compound produced in the preceding paragraph was resolved by HPLC on a semipreparative (20 cm×25 cm) Chiralpak AD column, using 2.5% isopropanol in hexane as the mobile phase, and a flow rate of 9 mL/min. The enantiomers were converted to their hydrochloride salts.

(+)-(endo)-3-(3-hexylsulfanyl-pyrazin-2-yloxy)-1-aza-bicyclo[2.2.1]heptane.

Melting point: 202°–204° C.

Optical Rotation: $[\alpha]_D^{25}$=+5, C=1.0, MeOH

Elemental analysis for $C_{16}N_{25}N_3OS.HCl$

Calculated: C, 55.87; H, 7.62; N, 12.21

Found: C, 55.35; H, 7.57; N, 12.01

(−)-(endo)-3-(3-hexylsulfanyl-pyrazin-2-yloxy)-1-aza-bicyclo[2.2.1]heptane.

Melting Point: 200°–202° C.

Optical Rotation: $[\alpha]_D^{25}$=−4.86, C=1.03, MeOH.

Elemental Analysis:

Calculated: C, 55.87; H, 7.62; N, 12.21

Found: C, 55.43; H, 7.62; N, 12.02

EXAMPLE 3

(−)-(endo)-3-(3-Hexylsulfanyl-pyrazin-2-yloxy-1-azabicyclo[2.2.1]heptane

Racemic (endo)-azabicyclo[2.2.1]heptan-3-ol (7.7g, 67 mmol) was dissolved in methylene chloride (40 mL) and added to a solution of L-(+)-tartaric acid (10.5 g) in a mixture of ethanol water (8:2 v/v) (100mL). The precipitated product was filtered and crystallized thrice from an ethanol water mixture (8:2 v.v).

The free base was liberated by dissolving the crystals in water, basifying with potassium carbonate and extracting with ethyl acetate. The solvent was evaporated and the residue crystallized to provide (−)-(endo)-azabicyclo[2.2.1] heptan-3-ol.

Optical Rotation: $[\alpha]_D^{25}$−4.0, C=0.508, $CH_2Cl_2$

Melting Point: 142°–144° C.

Hexanethiol (4.7 g, 40 mmole) was added to a slurry of sodium hydride (0.96 g) in THF (60 ml), and the mixture stirred for 30 minutes. The slurry was cooled to −5° C. and a solution of 2,3-dichloropyrazine (6 g) added. The mixture was stirred for 1.5 hours, filtered and the filtrate evaporated. The residue was purified by column chromatography on silica gel using varying concentrations of methanol in chloroform. Fractions containing the desired product were evaporated, yielding 2-chloro-3-hexylsulfanyl pyrazine. as an oil.

Mass spectral analysis: Molecular Weight by Electron Ionization M+M/Z=230/232 with a single chlorine atom.

A solution of (−)-endo-1-azabicyclo[2.2.1]heptane-3-ol (1.4 g, 123 mmole) in DMF (5 mL) was added to a suspension of sodium hydride (0.3 g, 12.5 mmole) in DMF (10 mL) and the mixture stirred at room temperature for 30 minutes. 2-Chloro-3-hexylsulfanyl pyrazine (2.6 g, 11.2 mmole) was dissolved in DMF (10 mL) and added. The mixture was stirred at room temperature for 2 hours. Isopropanol (2 mL) was added and the solvents evaporated. The residue was purfied via column chromatography using varying concentrations of methanol in chloroform. Fractions containing the product were combined and evaporated. The residue was dissolved in diethyl ether and treated with ethereal HCl, yielding the title compound as the hydrochloride salt, m.p. 204°–206° C.

Elemental Analysis for $C_{16}H_{25}N_3OS \cdot HCl$ Calculated: C, 55.58; H, 7.62; N, 12.22 Found: C, 55.73; H, 7.86; N, 12.10 Optical Rotation: $\alpha_D^{25}$–4.72, C=1.01, MeOH

EXAMPLE 4

(−)-(endo)-3-(3-Hexyloxy-pyrazin-2-yloxy)-1-azabicyclo[2.2.1]heptane

Hexanol was added to a slurry of sodium hydride in THF, and the mixture stirred for 30 minutes. The slurry was cooled to −5° C. and a solution of 2,3-dichloropyrazine added. The mixture was stirred for 1.5 hours, filtered and the filtrate evaporated. The residue was purified by column chromatography on silica gel using varying concentrations of methanol in chloroform. Fractions containing the desired product were evaporated, yielding 2-chloro-3-hexyloxy-pyrazine as an oil.

By replacing 2-chloro-3-hexylsulfanyl pyrazine in the preceding experiment with a molar equivalent amount of 2-chloro-3-hexyloxypyrazine and following the described procedure, the title compound was obtained as the hydrochloride salt, m.p. 172°–174° C.

Elemental analysis for $C_{16}H_{25}N_3O_2 \cdot HCl$ Calculated: C, 58.61; H, 7.99; N, 12.82 Found: C, 58.30 H, 8.19; N, 12.33 Optical Rotation: $[\alpha]_D^{25}$–5.84, C=1.02, MeOH

EXAMPLE 5

(+)-endo-3-(3-Hexyloxy-pyrazin-2-yloxy)-1-azabicyclo[2.2.1]heptane.

Racemic (endo)-azabicyclo[2.2.1]heptan-3-ol (7.7g, 67mmol) was dissolved in methylene chloride (40 mL) and added to a solution of (−)D-tartaric acid (10.5 g) in a mixture of ethanol water (8:2 v/v) (100mL). The precipitated product was crystallized thrice from an ethanol water mixture (8:2 v.v) $[\alpha]_D^{25}$+21.92; C=1, MeOH.

The free base was liberated by dissolving the crystals in water, basifying with potassium carbonate and extracting with ethyl acetate. The solvent was evaporated and the residue crystallized to obtain (+)(endo)-azabicyclo[2.2.1]heptane-3-ol.

Optical Rotation: $[\alpha]_D^{25}$+5.97, C=0.5, $CH_2Cl_2$

Melting Point: 142°–144° C.

Yield: 3.1 g

By replacing (−)(endo)-1-azabicyclo[2.2.1]heptan-3-ol in Example 3 with a molar equivalent of (+)-(endo)-1-azabicyclo[2.2.1]heptan-3-ol and using 2-chloro-3-hexyloxy-pyrazine instead of 2-chloro-3-hexylsulfanyl-pyrazine while following the procedure described in Example 3, the title compound was obtained as a hydrochloride salt, m.p. 172°–174° C.

Elemental analysis for $C_{16}H_{25}N_3O_2 \cdot HCl$ Calculated: C, 58.61; H, 7.99; N, 12.82 Found: C, 58.15; H, 7.96; N, 13.09 Optical Rotation: $[\alpha]_D^{25}$+7.89, C=1, MeOH

EXAMPLE 6

(exo)-3-(3-Hexylsulfanyl-pyrazin-2-yloxy)-1-azabicyclo[2.2.1]heptane

A solution of racemic (exo)-1-azabicyclo[2.2.1]heptane-3-ol (0.5 g, 44 mmole) in DMF (5 mL) was added to a suspension of sodium hydride (0.12 g, 5 mmole) in DMF (10 mL) and the mixture stirred at room temperature for 30 minutes. 2-Chloro-3-hexylsulfanyl pyrazine (1.0 g, 43 mmole) was dissolved in DMF (10 mL) and added. The mixture was stirred at room temperature for 2 hours. Isopropanol (2 mL) was added and the solvents evaporated. The residue was purified via column chromatography using varying concentrations of methanol in chloroform. Fractions containing the product were combined and evaporated. The residue was dissolved in diethyl ether and treated with ethereal HCl, yielding the title compound as the hydrochloride salt, m.p. 130°–132° C.

Elemental Analysis for $C_{16}H_{25}N_3OS \cdot HCl \cdot 0.5\ H_2O$ Calculated: C, 54.44; H, 7.71; N, 11.90 Found: C, 54.44; H, 7.85; N, 11.86

EXAMPLE 7

(+)-exo-3-(3-Hexylsulfanyl-pyrazin-2-yloxy)-1-azabicyclo[2.2.1]heptane

A solution of racemic (exo)-1-azabicyclo[2.2.1]heptan-3-ol in methylene chloride was added dropwise to a solution of L-(+)tartaric acid in an ethanol-water (80:20 v/v) mixture. The precipitate was filtered and solid recrystallized thrice from the ethanol-water mixture. The free base was liberated by basifying with potassium carbonate. The product was extracted using ethyl acetate. The solvent was evaporated and the residue crystallized from ethyl acetate to provide (+)-(exo)-azabicyclo[2.2.1]heptan-3-ol. Optical Rotation: $[\alpha]_D^{25}$+11.88, C=0.5, $CH_2Cl_2$.

By replacing racemic (exo)-1-azabicyclo[2.2.1]heptan-3-ol in Example 6 with a molar equivalent amount of (+)-(exo)-1-azabicyclo[2.2.1]heptan-3-ol and following the procedure described therein, the title compound was obtained as a hydrochloride salt, m.p. 132°–134° C.

Elemental Analysis for $C_{16}H_{25}N_3OS \cdot HCl \cdot 0.5\ H_2O$ Calculated: C, 54.44; H, 7.71; N, 11.90 Found: C, 54.81; H, 7.95; N, 11.81 Optical Rotation: $[\alpha]_D^{25}$+6.78, C=1.03, MeOH

EXAMPLE 8

(−)-(exo)-3-(3-Hexylsulfanyl-pyrazin-2-yloxy)-1-azabicyclo[2.2.1]heptane

A solution of racemic (exo)-1-azabicyclo[2.2.1]heptan-3-ol (4.7 g, 40 mmol) in methylene chloride (20 ml) was added dropwise to a solution of D(−)tartaric acid (6.3 g, 40 mmol) in an ethanol-water (80:20 v/v) mixture (25 ml). The precipitate was filtered and solid recrystallized thrice from the ethanol-water mixture. $[\alpha]_D^{25}$–1.3, C= 0.5, $CH_2Cl_2$. The free base was liberated by basifying with potassium carbonate. The product was extracted using ethyl acetate. The solvent was evaporated and the residue crystallized from ethyl acetate to yield (−)-exo-azabicyclo[2.2.1]heptan-3-ol, m.p. 129°–130° C.

Optical Rotation: $[\alpha]_D^{25}$–13.9, C=1.0, EtOH.

By replacing racemic (exo)-1-azabicyclo[2.2.1]heptan-3-ol with a molar equivalent of (−)-exo-1-azabicyclo[2.2.1]heptan-3-ol in Example 6, the title compound was obtained as the hydrochloride salt, m.p. 132°–134° C.

Elemental Analysis for $C_{16}H_{25}N_3OS.HCl.0.5H_2O$ Calculated: C, 54.44; H, 7.71; N, 11.92 Found: C, 54.71; H, 7.79; N, 12.45 Optical Rotation: $[\alpha]_D^{25}$−5.95, C=1.08, MeOH

EXAMPLE 9

(−)-(exo)-3-(3-Hexyloxy-pyrazin-2-yloxy)-1-azabicyclo[2.2.1]heptane

By replacing 2-chloro-3-hexylsulfanyl pyrazine in Example 8 with a molar equivalent amount of 2-chloro-3-hexyloxy pyrazine and following the procedure used therein, the title compound was obtained as the hydrochloride salt, m.p. 136°–137° C.

Elemental Analysis for $C_{16}H_{25}N_3O_2.2HCl.0.25 H_2O$ Calculated: C, 57.82; H, 8.04; N, 12.64 Found: C, 57.75; H, 7.82; N, 12.57 Optical Rotation: $[\alpha]_D^{25}$−15.87, C=1, MeOH

EXAMPLE 10

(+)-(exo)-3-(3-Hexyloxy-pyrazin-2-yloxy)-1-azabicyclo[2.2.1]heptane

By replacing (−)-(exo)-1-azabicyclo[2.2.1]heptan-3-ol in Example 6 with a molar equivalent amount of (+)-(exo)-1-azabicyclo[2.2.1]heptan-3-ol and replacing 2-chloro-3-hexylsulfanyl-pyrazine with 2-chloro-3-hexyloxy-pyrazine, the title product was obtained as the hydrochloride salt, m.p. 133°–135° C.

Elemental Analysis for $C_{16}H_{25}N_3O_2.HCl$ Calculated: C, 57.82; H, 8.04; N, 12.64 Found: C, 57.54; H, 8.23; N, 12.43 Optical Rotation: $[\alpha]_D^{25}$+16.26, C=1, MeOH

EXAMPLE 11

(exo)-3-(3-Hexyloxy-pyrazin-2-ylsulfanyl)-1-azabicyclo[2.2.1]heptane

A solution of racemic (exo)-1-azabicyclo[2.2.1]heptane-3-thiol (1.5 g, 13 mmole) in DMF (10 mL) was added to a suspension of sodium hydride (0.3 g, 13 mmole) in DMF (10 mL) and the mixture stirred at room temperature for 30 minutes. 2-Chloro-3-hexyloxy-pyrazine (2.3 g, 12 mmol) was dissolved in DMF (10 mL) and added, and the mixture stirred for 3 hours. The solvent was evaporated. The residue was treated with ethyl acetate and filtered. The filtrate was evaporated and the residue chromatographed on silica gel using varying concentrations of methanol in chloroform. The purified product was convened to the hydrochloride salt using saturated ethereal HCl, m.p. 165°–167° C.

Elemental Analysis for $C_{16}H_{25}N_3OS.HCl$ Calculated: C, 55.88; H, 7.62; N, 12.22 Found: C, 55.89; H, 7.70; N, 11.89

EXAMPLE 12

(exo)-3-(3-Hexylsulfanyl-pyrazin-2-ylsulfanyl)-1-azabicyclo-[2.2.1]heptane

By replacing 2-chloro-3-hexyloxypyrazine in Example 11 with a molar equivalent amount of 2-chloro-3-hexylsulfanylpyrazine and following the procedure described therein, the title compound was obtained as the oxalate salt from ethyl acetate solution, m.p. 106°–107° C.

Elemental Analysis for $C_{16}H_{25}N_3S_2.C_2H_2O_4.0.5 H_2O$ Calculated: C, 51.16; H, 6.68; H, 9.94 Found: C, 50.98; H, 6.66; N, 9.89

EXAMPLE 13

3-(3-Hexylsulfanyl-pyrazin-2-ylsulfanyl)-1-azabicyclo[2.2.2]octane

By replacing (exo)-1-azabicyclo[2.2.1]heptan-3-thiol in Example 11 with a molar equivalent of 1-azabicyclo[2.2.2]octane-3-thiol and following the procedure described therein, the title product was obtained as the hydrochloride salt, m.p. 104°–105° C.

Elemental Analysis for $C_{17}H_{27}N_3S_2.HCl.0.5 H_2O$ Calculated: C, 53.31; H, 7.63; N, 10.97 Found: C, 53.11; H, 7.67; N, 10.87

EXAMPLE 14

3-(3-Hexyloxy-pyrazin-2-ylsulfanyl)-1-azabicyclo[2.2.2]octane

By replacing racemic (exo) 1 azabicyclo[2.2.1]heptane-3-thiol in Example 11 with a molar equivalent amount of 1-azabicyclo[2.2.2]octane-3-thiol and following the procedure utilized therein, the title compound was obtained as the hydrochloride salt, m.p. 148°–150° C.

Elemental analysis for $C_{17}H_{27}N_3OS.HCl.0.5 H_2O$ Calculated: C, 55.63; H, 7.96; N, 11.45 Found: C, 55.84; H, 7.97; N, 11.47

EXAMPLE 15

3-(3-Hexyloxy-pyrazin-2-yloxyl-1-azabicyclo[2.2.2]octane

By replacing 1-azabicyclo[2.2.1]octane-3-thiol in Example 14 with a molar equivalent amount of 1-azabicyclo [2.2.2]octan-3-ol and following the procedure described there, the title compound was obtained as the hydrochloride salt, m.p. 161°–163° C.

Elemental Analysis for $C_{17}H_{27}N_3O_2.HCl.0.5 H_2O$ Calculated: C, 58.19; H, 8.33; N, 11.97 Found: C, 58.19; H, 8.33; N, 11.95

The affinity of the compounds of this invention for muscarinic receptors was established by testing them in accordance with the standard pharmacological test procedures in which the compound's ability to compete with [$^3$H]QNB binding and by analysis of PI hydrolysis stimulation in accordance with the following test procedures:

The binding affinity of the compounds of this invention at muscarinic receptor subtypes was determined by incubating triplicate samples of homogenized Chinese Hamster Ovary (CHO) cells which had been transfected with CMV vector containing cDNA expressing individual muscarinic receptor subtypes, for one hour at 37° C. with 0.23 nM radiolabeled quinuclidinyl benzilate [$^3$H]QNB, a representative compound of this invention, and a volume of 10 mM phosphate buffer to obtain a final incubation volume of 1000 µL. Vehicle and 2 µM atropine sulfate are substituted for the test solution to determine total and non-specific bindings, respectively. After incubation, the solutions are filtered and the filter paper is subjected to scintillation spectroscopy for radioactivity counting. Specific binding in the presence of the compound of this invention is expressed as a percentage of the atropine-sensitive binding. A concentration-response evaluation is obtained through non-linear regression analysis to obtain an $IC_{50}$ and/or Ki value. This procedure is based on that of Tonnaer et al, Life Sci., 40, 1981 (1987).

The ability of the compounds of this invention to stimulate hydrolysis of phosphoinositide (PI) in chinese Hamster Ovary (CHO) cells which had been transfected with CMV vector containing cDNA expressing $M_1$ acetylcholine receptors was determined in accordance with the procedure of El-Fakahany et al, J. Pharmacol. Exp. Ther. 257, 938 (1991), whereby PI hydrolysis is performed in reaction tubes, each containing 880 µL Kreb's Buffer, 10 µL of 1.0M LiCl solution, 10 µL of the compound representative of this invention or control vehicle, and 100 µL of CHO cell suspension in Kreb's Buffer (1,000,000 cells per mL). The tubes are incubated for one hour at 37° C. The reaction is quenched with chloroform and the phosphatidyl inositols are extracted with methanol and chloroform. Phase separation is assured with the addition of methanol and water followed by centrifugation. The tritiated inositol phosphates are recovered on BioRad AG 1-X8 anion exchange resin in the formate cycle. After washing the resin with water and myo-inositol, the inositol phosphates are eluted with ammonium formate/formic acid, collected and subjected to liquid scintillation spectroscopy. The results are expressed as a percentage of the mean value obtained for carbachol ($EC_{50}$= 8.0 µM).

The appended tables contain the Biological data. Table (1) displays results of the Muscarinic binding studies, and Table (2) the Functional selectivity. Cloned human receptors in CHO cells were used in these studies.

The results of these studies are given below:

TABLE 1

| Example | [$^3$H]QNBinding Ki(µM)$m_1$ | [$^3$H]QNB Binding Ki(µM)$m_2$ | $m_1$CHO @ 30 × Ki % Carbachol |
| --- | --- | --- | --- |
| 1 | 0.03 | 0.02 | 101.8 |
| 2 | 0.0067 | 0.013 | 97.1 |
| 2(+) | 0.027 | 0.063 | 31.1 |
| 2(−) | 0.002 | 0.0045 | 46.5 (at Ki) |
| 4 | 0.032 | 0.024 | 75 |
| 5 | 0.083 | 0.071 | 51 |
| 6 | 0.123 | 0.088 | 104.0 (at Ki) |
| 7 | 0.075 | 0.059 | 107.3 (at Ki) |
| 8 | 0.124 | 0.008 | 44.2 (at Ki) |
| 9 | 0.69 | 0.774 | 56 |
| 10 | 0.465 | 0.149 | 9 |
| 11 | 0.292 | — | 41.6 (at Ki) |
| 12 | 0.030 | 0.064 | 62 |
| 13 | 0.029 | — | 45.9 |
| 14 | 0.076 | — | 29.5 (at Ki) |
| 15 | 0.14 | 0.124 | 59.6 (at Ki) |

TABLE 2

| Example | $m_1$ agonism [P.I.] $EC_{50}$ (nM) | $m_2$ agonism (cAMP) $EC_{50}$ (nM) | Functional Selectivity-$m_2/m_1$ |
| --- | --- | --- | --- |
| 2(−) | 0.4 | 16 | 40 |
| 7 | 10.3 | 2400 | 240 |
| 4 | 5.5 | | |

Hence, the compounds of this invention demonstrated high affinity for muscarinic receptors (especially the ml receptor) and are therefore useful in the treatment of disease states associated with insufficient cerebral acetylcholine production or release.

Based upon this receptor binding information and PI hydrolysis, the compounds of this invention are characterized as useful in the treatment of cognitive disorders associated with decreased levels of cerebral acetylcholine production or release, such as presenile dementia, senile dementia of the Alzheimer's type, Parkinson's disease, Down's Syndrome and dementia pugilistica.

As such, the compounds may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from cerebral acetylcholine insufficiency must be subjectively determined by the attending physician. The variables involved include the severity of the dysfunction, and the size, age and response pattern of the patient.

What is claimed is:

1. A compound of the formula:

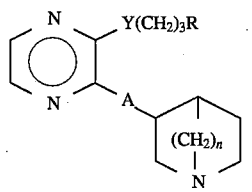

in which Y is oxygen or sulfur;

A is oxygen, sulfur or —NR$_2$, where R$_2$ is hydrogen or alkyl of 1 to 6 carbon atoms;

R is —CH$_2$CH$_3$, —CH$_2$CH$_2$CH$_3$, —CH(CH$_3$)$_2$, —CH$_2$CH(CH$_3$)$_2$, —CH$_2$CF$_3$, —CH$_2$CH$_2$CF$_3$, —CH(CF$_3$)$_2$, —CH$_2$CH(CF$_3$)$_2$, —C$_6$H$_5$ or —CH$_2$C$_6$H$_5$;

and n is one of the integers 1 or 2;

or a pharmaceutically acceptable salt thereof.

2. A compound of claim 1 in which A and Y are oxygen or sulfur, R is propyl and n is 1.

3. A levo isomer of claim 2, of endo configuration, in which A is oxygen and Y is sulfur.

4. A dextro isomer of claim 2, of endo configuration, in which A and Y are oxygen.

5. A dextro isomer of claim 2, in which A is oxygen and Y is sulfur.

6. The compound of claim 1 which is (endo)-3-(3-hexyloxy-pyrazin-2-yloxy)-1-aza-bicyclo[2.2.1]heptane or a pharmaceutically acceptable salt thereof.

7. The compound of claim 1 which is (endo)-3-(3-hexylsulfanyl-pyrazin-2-yloxy)-1-aza-bicyclo[2.2.1] heptane or a pharmaceutically acceptable salt thereof.

8. The compound of claim 1 which is (+)-(endo)-3-(3-hexylsulfanyl-pyrazin-2-yloxy)-1-aza-bicyclo[2.2.1 ]heptane or a pharmaceutically acceptable salt thereof.

9. The compound of claim 1 which is (−)-(endo)-3-(3-hexylsulfanyl-pyrazin-2-yloxy)-1-aza-bicyclo[2.2.1 ]heptane or a pharmaceutically acceptable salt thereof.

10. The compound of claim 1 which is (−)-(endo)-3-(3-hexyloxy-pyrazin-2-yloxy-1-azabicyclo[2.2.1] heptane or a pharmaceutically acceptable salt thereof.

11. The compound of claim 1 which is (+)-endo-3-(3-hexyloxy-pyrazin-2-yloxy)-1-azabicyclo[2.2.1] heptane or a pharmaceutically acceptable salt thereof.

12. The compound of claim 1 which is (exo)-3-(3-hexylsulfanyl-pyrazin-2-yloxy)-1-azabicyclo[2.2.1]heptane or a pharmaceutically acceptable salt thereof.

13. The compound of claim 1 which is (+)-exo-3-(3-hexylsulfanyl-pyrazin-2-yloxy)-1-azabicyclo[2.2.1] heptane or a pharmaceutically acceptable salt thereof.

14. The compound of claim 1 which is (−)-exo-3-(3-hexylsulfanyl-pyrazin-2-yloxy)-1-azabicyclo[2.2.1] heptane or a pharmaceutically acceptable salt thereof.

15. The compound of claim 1 which is (−)-(exo)-3-(3-hexyloxy-pyrazin-2-yloxy)-1-azabicyclo[2.2.1] heptane or a pharmaceutically acceptable salt thereof.

16. The compound of claim 1 which is (+)-(exo)-3-(3-hexyloxy-pyrazin-2-yloxy)-1-azabicyclo[2.2.1] heptane or a pharmaceutically acceptable salt thereof.

17. The compound of claim 1 which is (exo)-3-(3-hexyloxy-pyrazin-2-ylsulfanyl)-1-azabicyclo[2.2.1]heptane or a pharmaceutically acceptable salt thereof.

18. The compound of claim 1 which is (exo)-3-(3-hexylsulfanyl-pyrazin-2-ylsulfanyl)-1-azabicyclo-[2.2.1] heptane or a pharmaceutically acceptable salt thereof.

19. The compound of claim 1 which is 3-(3-hexylsulfanyl-pyrazin-2-ylsulfanyl)-1-azabicyclo[2.2.2]octane or a pharmaceutically acceptable salt thereof.

20. The compound of claim 1 which is 3-(3-hexyloxy-pyrazin-2-ylsulfanyl)-1-azabicyclo[2.2.2]octane or a pharmaceutically acceptable salt thereof.

21. The compound of claim 1 which is 3-(3-hexyloxy-pyrazin-2-yloxy)-1-azabicyclo[2.2.2]octane or a pharmaceutically acceptable salt thereof.

22. A compound of claim 1 which is:

(±)-(endo)-3-(3-hexyloxy-pyrazin-2-yloxy)-1-aza-bicyclo[2.2.1]heptane;

(endo)-3-(3-hexylsulfanyl-pyrazin-2-yloxy)-1 -aza-bicyclo[2.2.1]heptane;

(+)-(endo)-3-(3-hexylsulfanyl-pyrazin-2-yloxy)-1-aza-bicyclo[2.2.1]heptane;

(−)-(endo)-3-(3-hexylsulfanyl-pyrazin-2-yloxy)-1-aza-bicyclo[2.2.1]heptane;

(−)-(endo)-3-(3-hexyloxy-pyrazin-2-yloxy-1-azabicyclo [2.2.1]heptane;

(+)-endo-3-(3-hexyloxy-pyrazin-2-yloxy)-1 -azabicyclo [2.2.1]heptane;

(+)-exo-3-(3-hexylsulfanyl-pyrazin-2-yloxy)-1-azabicyclo[2.2.1]heptane;

(exo)-3-(3-hexylsulfanyl-pyrazin-2-ylsulfanyl)-1-azabicyclo-[2.2.1]heptane;

3-(3-hexylsulfanyl-pyrazin-2-ylsulfanyl)-1-azabicyclo [2.2.2]octane; or 3-(3-hexyloxy-pyrazin-2-ylsulfanyl)-1-azabicyclo[2.2.2] octane;

or a pharmaceutically acceptable salt thereof.

23. A method of alleviating the symptoms of memory loss attending senility which comprises administering to a patient in need thereof, parenterally or orally, a muscarinic receptor active compound of the formula:

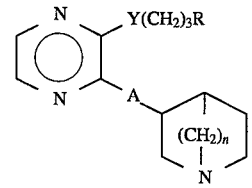

in which Y is oxygen or sulfur;

A is oxygen, sulfur or —NR$_2$, where R$_2$ is hydrogen or alkyl of 1 to 6 carbon atoms;

R is —CH$_2$CH$_3$, —CH$_2$CH$_2$CH$_3$, —CH(CH$_3$)$_2$, —CH$_2$CH(CH$_3$)$_2$, —CH$_2$CF$_3$, —CH$_2$CH$_2$CF$_3$, —CH(CF$_3$)$_2$, —CH$_2$CH(CF$_3$)$_2$, —C$_6$H$_5$ or —CH$_2$C$_6$H$_5$;

and n is one of the integers 1 or 2;

or a pharmaceutically acceptable salt thereof, in an amount sufficient to enhance cognition.

* * * * *